United States Patent [19]

Graefje et al.

[11] 4,153,425

[45] May 8, 1979

[54] ω-DISUBSTITUTED AMINO ALKANOIC ACID-N-AMIDES AS FUEL ADDITIVES

[75] Inventors: Heinz Graefje, Ludwigshafen; Guenther Nottes, Limburgerhof; Herbert Mueller, Frankenthal; Guenther Daumiller, Ziegelhausen; Herwig Hoffmann, Frankenthal, all of Fed. Rep. of Germany

[73] Assignee: BASF Aktiengesellschaft, Ludwigshafen, Fed. Rep. of Germany

[21] Appl. No.: 697,771

[22] Filed: Jun. 21, 1976

[30] Foreign Application Priority Data

Jul. 15, 1975 [DE] Fed. Rep. of Germany ....... 2531469

[51] Int. Cl.[2] ...................... C10L 1/18; C07C 103/18; C10L 1/22

[52] U.S. Cl. .................................. 44/71; 260/558 A; 260/561 A; 260/562 N

[58] Field of Search ........... 44/71; 260/558 A, 561 A, 260/562 N

[56] References Cited

U.S. PATENT DOCUMENTS

| | | | |
|---|---|---|---|
| 2,580,411 | 1/1952 | Cusic | 260/561 A |
| 2,921,085 | 1/1960 | Schremm | 260/561 A X |
| 2,968,618 | 1/1961 | Thompson | 44/71 X |
| 2,968,629 | 1/1961 | Thompson | 44/71 X |
| 3,277,118 | 10/1966 | Schmid et al. | 260/561 A X |
| 3,779,724 | 12/1973 | Kerschner et al. | 44/71 X |
| 3,867,405 | 2/1975 | Kanetka et al. | 260/561 A X |
| 4,047,900 | 9/1977 | Dorn et al. | 44/71 X |

OTHER PUBLICATIONS

A.P.C., Application of Hentrich et al., Ser. No. 427,064

*Primary Examiner*—Thomas Waltz

*Attorney, Agent, or Firm*—Keil & Witherspoon

[57] ABSTRACT

The novel compounds ω-N-disubstituted aminoalkanoic acid N'-amides of the formula

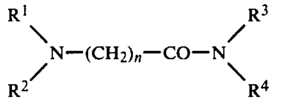

I, in which $R^1$, $R^2$, $R^3$ and $R^4$ are identical or different and denote branched-chain or straight-chain alkyl radicals of from 7 to 20 carbon atoms, $R^2$ and $R^4$ may also denote a preferably mononuclear aralkyl or aryl radical and n denotes an integer of from 3 to 5, the total number of carbon atoms in the radicals $R^1$ to $R^2$ and in $R^3$ and $R^4$ being at least 16, are added in small quantities to gasoline and effect cleaning of the carburetor and obviate the formation of deposits on the valves.

3 Claims, No Drawings

ω-DISUBSTITUTED AMINO ALKANOIC ACID-N-AMIDES AS FUEL ADDITIVES

This invention relates to ω-N-disubstituted aminoalkanoic acid N-amides containing radicals having at least 7 carbon atoms, to a process for the manufacture of said compounds and to the use of said compounds as additives for internal combustion engine fuels.

The increasing density of city and road traffic is a cause of atmospheric pollution due to partially burned or unburned portions of fuels emanating from the automobile engines. An important casual factor in the incomplete combustion of gasoline hydrocarbons and of lubricating oil mists is the occurrence of unduly rich mixtures produced by impurities and deposits in the carburetors. In the more recent automobile engines, in particular, the oil sump is vented with recycling of the so-called blow-by gas to the suction side or air filter of the carburetor. Although this causes a portion of the oil mists which form in the oil sump to be sucked through the carburetor to the engine, where said oil is burned for the most part, portions of said oil become deposited in the cavities of the carburetor and in the inlet channels and on the inlet valves. Modern high-performance carburetors are complicated structures having very fine channels and bores and accurately calibrated nozzles for atomizing and metering the gasoline. Only slight deposits of dirt and residues in the fine regulators, nozzles and channels of these carburetors are sufficient to impair the performance of the carburetors. As a result, the composition of the fuel/air mixture is incorrect and combustion in the engine is thus not so complete as when the carburetors are clean. The exhaust gases then contain, as mentioned above, partially burned and unburned hydrocarbon residues. At the same time, the ratio of carbon monoxide to carbon dioxide in the exhaust gases is adversely affected, i.e. the proportion of carbon monoxide is greater when the carburetor is dirty.

A large number of surface active compounds which are soluble in gasoline or oil has been proposed for this purpose. Examples are derivatives of higher fatty acids such as oleic acid, palmitic acid, palm kernel oil fatty acid, fish oil acid and naphthenic acid, in which the number of carbon atoms ranges from about 10 to 20. It has also been recommended to use condensates of fatty acids, fatty acid esters, fatty acid amides and mixtures thereof.

Although some of these products show a good cleaning effect in the carburetor, they suffer from the disadvantage that they deposit the dirt which they have removed from the carburetor onto the hot inlet valves, where said dirt decomposes or carbonizes to cause said inlet valves to stick or, in particularly bad cases, to cease operating entirely.

It is thus very important to find additives for gasoline which clean the carburetor and inlet channels and also show no tendency to decompose or become deposited on the very hot inlet valves. Although such demands could be realized in some cases, it has not always been possible to combine both properties, i.e. efficient cleaning of the carburetor and low decomposability or even cleaning of the valves. There is thus a need for substances which are capable of cleaning the carburetor satisfactorily and, in particular, are stable at the high temperatures encountered at the inlet valves and are capable of preventing deposition at said valves or of reducing or completely removing any deposits already present on said valves. Another requirement is that these compounds should burn away substantially completely in the engine.

It is thus an object of the present invention to provide novel compounds which, when dissolved in gasoline in small quantities, meet the above requirements.

We have now found that ω-N-disubstituted aminoalkanoic acid N'-amides of the formula

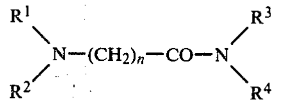

I, in which $R^1$, $R^2$, $R^3$ and $R^4$ are the same or different and denote branched-chain or straight-chain alkyl of from 7 to 20 carbon atoms, $R^2$ and $R^4$ may also denote aryl or aralkyl, preferably phenyl, alkylphenyl or benzyl, and n is a number from 3 to 5, the total number of carbon atoms in $R^1$ and $R^2$ or in $R^3$ and $R^4$ being at least 16, show very good valve-cleaning properties when dissolved in small amounts in fuels for internal combustion engines.

In the compounds of formula I, the radicals $R^1$, $R^2$ and $R^3$ and $R^4$ are preferably identical and contain, in particular, from 12 to 18 carbon atoms and preferably from 12 to 14 carbon atoms. We generally prefer those compounds of this nature which have a molecular weight of at least 500. The upper limit of the chain length of the radicals R is determined only by practical considerations relating to the reaction rate at which such high molecular weight secondary amines may be synthesized. This limit usually lies at C 20.

The amines R—NH—R to be used in the preparation of ω-dialkyl amino alkanoic acid dialkylamines may have radicals having linear or branched chains. In the latter case, the compounds of formula I are equally effective but show the advantage of having low viscosities and low pour points. It will be appreciated that the starting products preferred are amines which may be readily obtained from commercially available materials. Examples are the catalytic reaction of alcohols with ammonia, hydrogenating amination of aldehydes and the hydrogenation of nitriles. It is well known that all of these reactions may be controlled so as to produce mainly secondary amines.

Examples are:

| | | |
|---|---|---|
| dilauryl amine | $(C_{12}H_{25})_2$ NH | unbranched |
| ditridecylamine | $(C_{13}H_{27})_2$ NH | branched |

The said ditridecylamine is an isomer mixture obtained from tetramer propylene via the $C_{13}$ alcohol mixture and containing, inter alia, di-(tetramethylnonyl)-amine and di-(trimethyldecyl)-amine.

| | | |
|---|---|---|
| Di(pentamethyloctyl)-amine | $(C_{13}H_{27})_2$ NH | branched |
| dipalmitylamine | $(C_{16}H_{33})_2$ NH | unbranched |
| distearylamine | $(C_{18}H_{37})_2$ NH | unbranched |
| di-($C_{13-15}$ alkyl)-amine | $(C_{14}H_{29})_2$ NH | slightly branched |

The last-named amine is a mixture of dialkylamines having from 13 to 15 carbon atoms in the alkyl radicals. Tests carried out using such mixtures showed that the amines used need not be very pure substances. However, they should not contain impurities having condensable groups such as monoalkyl amines. On the other hand, minor quantities of trialkylamines have no disturbing effect either in the preparation of the compounds of formula I or in their use as gasoline additives.

Also suitable as starting materials are mixed amines such as N-benzylstearylamine, $C_{18}H_{37}$—NH—$C_7H_7$, N-stearylaniline, N-palmityltoluidine and similar substances which, however, are more difficult to obtain on an industrial scale.

Preparation of the ω-N-disubstituted aminolkanoic acid-N'-amides of formula I may be effected in known manner by reaction of substantially stoichiometric amounts of amines of the formulae $R^1$—NH—$R^2$ and $R^3$—NH—$R^4$ with caprolactone, valerolactone and, preferably, butyrolactone at temperatures of from 150° to 300° C. and at atmospheric or elevated pressure, e.g. pressures of up to 50 bars.

The manufacture of low molecular weight compounds from butyrolactone, which are similar to those of formula I, is described in German Pat. Nos. 882,093 and 1,211,652. According to these patents, δ-butyrolactone is reacted with twice the molar amount or an excess of a low molecular weight amine under pressure and with catalysis by acids or aluminum oxide.

If these methods are used for the manufacture of compounds of formula I in which the amines have 16 or more carbon atoms, these compounds are also formed but only at less satisfactory degrees of conversion as compared with compounds having relatively low molecular weights. At relatively high molecular weights, the separation of the reaction mixtures is thus more difficult.

We have now found that the reaction of butyrolactone with high molecular weight amines produces compounds of formula I also with virtually complete conversion of said amines and with particularly easy working up of the reaction mixture if, contrary to the teaching of the cited patent specifications, use is made of an excess of butyrolactone, for example from 3 to 10 moles and preferably from 4 to 6 moles of butyrolactone per mole of amine. The addition of acids is completely unnecessary and the reaction may be carried out at atmospheric pressure and at temperatures as low as from 180° to 200° C. (Although the reaction may be carried out at subatmospheric or superatmospheric pressure on an industrial scale, this provides no added advantage.) During the reaction, the water of reaction and small amounts of butyrolactone distill off. The excess butyrolactone may, on completion of the reaction after, say, from 15 to 40 hours of reaction time, be recovered by distillation under reduced pressure.

Although the aforementioned method of preparation is preferred, the compounds of formula I may be equally well manufactured in known manner by reaction of amines $R^1$—NH—$R^2$ and $R^3$—NH—$R^4$ with ω-chloroalkanoic esters or ω-chloroalkanoic chlorides.

Specific examples of said compounds are:

di-tridecylaminobutyroditridecylamide
di-dodecylaminobutyrodidodecylamide
di-oleylaminobutyrodioleylamide
di-stearylaminobutyrodistearylamide
di-palmitylbutyrodipalmitamide Our novel compounds may be used as additives for gasoline either alone or together with, say, less heat-resistant carburetor scavengers. The fuels may also contain other conventional additives such as antiicing and anticorrosive agents.

Our novel gasoline additives are added to gasoline in amounts os usually from 10 to 2,000 ppm and preferably from 50 to 200 ppm.

By gasolines, i.e. fuels for internal combustion engines, we mean mixtures of technical hydrocarbons having boiling points between from about 40° to 200° C. These include hydrocarbons commencing at, say, butane or isobutane and continuing through $C_5$ and $C_6$ hydrocarbons up to about $C_{12}$ hydrocarbons. These technical mixtures contain, of course, both aliphatic and isoparaffinic, aromatic, alkylaromatic and so-called naphthene-base hydrocarbons. Naphthene-base hydrocarbons consist of mixtures of five- and six-membered cyclic compounds, which may contain side chains. Furthermore, these technical hydrocarbon mixtures also contain olefins having the same number of carbon atoms as mentioned above. Mixtures of lead tetraethyl and lead tetramethyl are also added to the gasolines in order to raise the octane number.

The good effect of compounds of formula I is not limited to gasolines used in automobiles. It has been found that these compounds may also be used in aeroplane gasolines, particularly for use in aeroplane piston engines. The compounds of the invention are not only effective in carburetors but also in the injection units of injection motors.

An important technical advantage of the present invention is that the aminoalkanoic amides of formula I surprisingly show a property not possessed by the prior art additives. It is well known that fuels or internal combustion engines are very frequently supplemented by both alcoholic additives to prevent icing of the carburetor and other amine-containing additives acting as scavenging substances soluble in gasoline. In such cases, difficulties may occur when water or even just moisture enters the gasoline supply system, such as may occur by condensation of atmospheric moisture in the fuel tank or by entrainment of water residues. In this case, the prior art additives accelerate corrosion of the metals, particularly the light metal alloys, from which the automobile carburetors are made. The resulting magnesium, aluminum and other metal hydroxides, carbonates and oxide layers become detached from the walls of the carburetor thus increasing the possibility of attack on the material of the carburetor. This may lead to blockage of the fine carburetor channels, whilst other pipes such as those of copper and alloys thereof, may also be attacked. Hitherto, it has been necessary to accept the great drawback of having to add special anticorrosive substances to the fuels or gasolines. However, such inhibitors, for example sodium nitrite or sulfuryl substances such as thiourea and its derivatives, are either insoluble in gasoline or cause the fuel to contain sulfur or nitrogen, which substances contribute to air pollution. We have found, surprisingly, that the aminoalkanoic amides claimed in the present invention do not attack the light metal alloys of which the automobile carburetors are usually made and, furthermore, even provide a certain degree of protection against corrosion by moisture, alcohols and polyglycol-containing additives for the prevention of carburetor icing.

This is illustrated by the Table below.

TABLE

| Carburetor material additive to gasoline + $H_2O$ | $ZnAl_4Cu_1$ alloy weight loss |
|---|---|
| Control (no additive) | 208 mg |
| 50 mg of A | 150 mg |

TABLE-continued

| Carburetor material additive to gasoline + $H_2O$ | $ZnAl_4Cu_1$ alloy weight loss |
|---|---|
| 500 mg of A | 90 mg |
| 1,000 mg of A | 70 mg |
| 1,500 mg of A | 46 mg |
| 2,000 mg of A | 31 mg |

A = di-tridecylamino-butyroditridecylamide.

Small plates measuring 50 × 50 × 2 mm of the same alloy as used for making the carburetor are placed in a 250 ml wide-neck glass flask after they have been slightly roughened with emery paper and weighed. For each test, 100 ml of gasoline containing the product to be tested and 4 ml of condensed water are thoroughly mixed by means of a turbine stirrer so as to provide a very fine suspension of the water in the gasoline.

This mixture is then poured into the wide-neck glass flasks. A mist of very fine water particles soon settles on the plates of light metal and over a period of time the base of the flasks also becomes covered with separated water. After 2 weeks, the light metal plates are removed from the flasks and thoroughly rinsed with water and any sediments thereon are removed by light rubbing with the finger. They are then dried with acetone. The differences in weight compared with the control value give an indication of the attacking action of the corrosive components or the protective action of the compounds of the invention compared with products used hitherto.

A = di-tridecylamino-butyroditridecylamide
B = di-dodecylamino-butyrodidodecylamide
C = di-palmitylamino-butyrodipalmitylamide
D = di-stearylamino-butyrodistearylamide
Carburetor material: $ZnAl_4Cu_1$ alloy

| Additive to gasoline + $H_2O$ | Weight loss |
|---|---|
| Control (no additive) | 208 mg |
| 2,000 mg of A | 31 mg |
| 2,000 mg of B | 42 mg |
| 2,000 mg of C | 57 mg |
| 2,000 mg of D | 47 mg |

MANUFACTURING EXAMPLE 1

1 mole of ditridecylamine (isomer mixture $C_{26}H_{55}N$) and 5 moles of butyrolactone are heated for 30 hours at 200° C. in a stirred vessel. Over this period, 1 mole of water and about 0.5 mole of butyrolactone distill off. Following distillation of the excess butyrolactone at 20 mm of Hg there is obtained 0.5 mole of δ-di-tridecylaminobutyroditridecylamide. The product contains less than 0.5% of ditridecylamine.

Comparative Examples: When the molar ratio of butyrolactone to ditridecylamine is 2:1 the conversion of the amine is only 78% after 30 hours and only 68% when the molar ratio is 1:1. Neither can the degree of conversion be raised by the use of very much longer reaction times.

If the excess of lactone is replaced by similar solvents such as N-methylpyrrolidone, such dilution is found to be ineffective. The conversions obtained are from 30 to 40%. The Example clearly shows that the optimum reaction temperatures are at about the boiling point of the lactone.

APPLICATION EXAMPLE (a)

A metal block is ground so as to have recesses exactly corresponding to the valve seatings of an automobile engine. Small iron plates corresponding to the head of a valve are fitted into said recesses. When the block is heated electrically the fitted iron plates may also be heated. A sufficient quantity of the substance to be tested is placed in the plates to enable the end of the mercury bulb of a thermometer to be immersed therein, for example 1,000 mg. By heating the metal block electrically, any desired temperatures between 250° and 350° C. may be thermostatically controlled and maintained over long periods.

The plates are weighed before and after thermal treatment, and the resulting difference in weight after, say, 10 minutes at 350° C. gives the loss of weight by decomposition. In the case of unsuitable substances, the residues remaining after the thermal treatment are carbonized to such an extent that they are then no longer soluble in lubricating oil. In the case of compounds of the invention, however, the residues remaining after said thermal treatment are substantially soluble in a lubricating oil.

It is also possible to mix the aminoamides of the invention with the aforementioned di- and tri-oleic acid amides to give residues formed after the thermal treatment which are capable of being removed by lubricating oil.

Some results are listed in the Table below:

| Treatment time 10 min. at 350° C. | Initial weight 1,000 mg residual weight | Residual weight after washing with oil (insoluble residue) |
|---|---|---|
| di-tridecyl-aminobutyroditridecylamide | 261 mg. | 0-1 mg |
| di-palmityl-aminobutyrodipalmitylamide | 526 mg | 12 mg |
| di-octyl-aminobutyrodioctylamide | 132 mg | 32 mg |
| di-dodecyl-aminobutyrodidodecylamide | 197 mg | 1 mg |
| di-stearyl-aminobutyrodistearylamide | 673 mg | 21 mg |
| di-tetradecyl-aminobutyroditetradecylamide | 275 mg | 0-1 mg |

The following substances were subjected to a plate test in a manner similar to that described above. In each case, 1,000 mg of substance were treated at 350° C. until the residue began to thicken and assume a brownish color. In each case, a portion of the substance evaporated.

| | Time | Residue (mg) |
|---|---|---|
| ditridecylamino-valeroditridecylamide | 17′ | 101.5 |
| ditridecylamino-caproditridecylamide | 19′ | 155 |
| ditridecylamino-butyroditridecylamide | 25′ | 143.7 |

EXAMPLE (b)

A BASF single-cylinder test engine having a cubic capacity of 332 $cm^3$ (cylinder diameter = 65 mm, stroke = 100 mm) was run over periods of 50 hours at a constant speed of 2,000 rpm and a fuel rate of 1.6 l per hour. The engine was modified so as to return 10% of the exhaust gases to the crank case below the level of the oil, from which it was passed to the air filter of the suction line of the carburetor (Solex type 26VFIS).

The automobile gasoline used was one consisting of a mixture of catalytically cracked gasoline, platformate, straight-run gasoline, and 5% of pyrolysis gasoline having the usual lead content. The engine was opened up on completion of the test run. The inlet valve was found to be covered with asphalt-like or coke-like residues. This deposit was carefully removed and the difference in weight between the polluted and cleaned inlet valve was found to be 164 g.

However, when 1,000 mg/l of ditridecylamino-butyroditridecylamide were added to the gasoline prior to the test run, the valve was found to be covered by only a small amount of asphalt-like residue on completion of the run, the valve shaft being clean. The residue, determined from the difference in weight of the inlet valve before and after cleaning, was found to weight 26 g.

The corresponding weight found on using 1,000 mg/l of ditetradecylamino-butyroditetradecylamide was 32 g. The valve shaft and the appearance of the inlet valve were found to be very good.

EXAMPLE (c)

2 automobiles of the 2.5-liter class and of the same type and manufacture which had covered approximately the same distance (± 9,000 km) were operated simultaneously as taxis in the same town using the same premium gasoline and the same lubricating oil. The automobiles had previously been driven 72,000 and 81,000 km respectively and they were in very good condition, particularly as regards their engines.

The first automobile was operated on gasoline containing no additive and was found, after having being driven for 15,000 km, to show no reduction in the usual blackish deposits in the carburetor and mixture inlet system. The valves were found to be covered with thick deposit. When ditridecylamine-butyroditridecylamide was added to the fuel of the second vehicle in amounts of 70 ppm to 100 ppm, a distinct reduction of the previously formed deposits on the inlet valves could be observed after driving the car for a further 3,000 km. After a further 5,000 km approximately, the deposit on the inlet valves disappeared almost completely. The inlet valves were clean.

EXAMPLE (d)

A Fiat engine type 500 D having a Weber carburetor was idled on an engine test bench. At the beginning of the test, the fuel/air mixture was regulated so as to give an exhaust gas containing from 3.6 to 4.4% by volume of carbon monoxide. The temperature of the cooling water was held at 47°±1° C. The fuel used was a stabilized gasoline having a lead content of 0.4 g/l and containing portions of cracked gasoline.

During the tests carried out with said fuel, the carbon monoxide content of the exhaust gas increased with time, this being due to deposits in the carburetor and on the inlet valves.

After a test run of 100 hours, the engine was opened up and the inlet valves were found to be extensively polluted. Even the valve shafts showed asphalt-like deposits. However, when 500 ppm of didodecylamino-butyrodidodecylamide were added to the fuel and the engine was run under identical conditions, no growth of deposits on the inlet valves could be observed even after a test run of 200 hours. The valve shafts were also very clean.

We claim:

1. A composition of matter comprising predominantly gasoline for Otto cycle engines and an amount effective for cleaning Otto cycle engine carburetors of an ω-N-disubstituted aminoalkanoic acid N'-diamide of formula

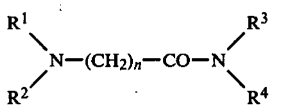

I, in which each of $R^1$, $R^2$, $R^3$ and $R^4$ represents branched-chain or straight-chain alkyl of from 7 to 20 carbon atoms, $R^2$ and $R^4$ may also denote phenyl, alkyl-substituted phenyl and benzyl, the total number of carbon atoms in $R^1$ and $R^2$ and in $R^3$ and $R^4$ being at least 16 in each case, and n is a number from 3 to 5.

2. A composition of matter as set forth in claim 1 and comprising gasoline with a content of from about 10 to 2,000 ppm by weight of an ω-N-disubstituted aminoalkanoic acid N'-diamide of formula I.

3. A composition of matter as set forth in claim 2 wherein each of the alkyl radicals $R^1$, $R^2$, $R^3$ and $R^4$ contains from 12 to 18 carbon atoms.

* * * * *